United States Patent [19]
Olson et al.

[11] Patent Number: 5,364,797
[45] Date of Patent: Nov. 15, 1994

[54] SENSOR DEVICE CONTAINING MESOPOROUS CRYSTALLINE MATERIAL

[75] Inventors: David H. Olson, Pennington, N.J.; Galen D. Stucky, Santa Barbara, Calif.; James C. Vartuli, West Chester, Pa.

[73] Assignee: Mobil Oil Corp., Fairfax, Va.

[21] Appl. No.: 64,280

[22] Filed: May 20, 1993

[51] Int. Cl.$^5$ .................... B01J 29/00; C12Q 1/00; G01N 21/00; G01N 27/00; G01N 31/00; G01N 33/00; G01N 33/20; G01N 33/53

[52] U.S. Cl. .................... 436/501; 422/55; 422/82.01; 422/82.05; 422/83; 423/118.1; 423/328.2; 423/329.1; 435/4; 435/6; 435/7.1; 436/73; 436/86; 436/100; 436/103; 436/106; 436/119; 436/124; 436/127; 436/139; 436/149; 436/163; 436/164; 436/524; 502/64; 502/77

[58] Field of Search .............. 422/68.1, 82.05, 82.01, 422/82.08, 55, 83; 436/166, 169, 149, 501, 163, 527, 164, 524, 100, 103, 106, 119, 124, 127, 139, 149, 76, 73; 502/60, 64, 77; 423/326, 328, 329, 330-332, 118, 277, 328.1, 328.2, 329.1; 435/4, 6, 7.1

[56] References Cited

U.S. PATENT DOCUMENTS

| | | | |
|---|---|---|---|
| 4,876,890 | 10/1989 | Mercer et al. | 73/336.05 |
| 4,931,851 | 6/1990 | Sibbald et al. | 257/414 |
| 5,057,296 | 10/1991 | Beck | 423/277 |
| 5,057,430 | 10/1991 | Newman | 435/288 |
| 5,057,431 | 10/1991 | Lubbers et al. | 435/288 |
| 5,057,436 | 10/1991 | Ball | 436/113 |
| 5,078,856 | 1/1992 | Yamaguchi et al. | 204/418 |
| 5,078,885 | 1/1992 | Mochizuki et al. | 204/418 |
| 5,098,684 | 3/1992 | Kresge et al. | 423/718 |
| 5,102,643 | 4/1992 | Kresge et al. | 423/702 |
| 5,143,879 | 9/1992 | Whitehurst | 502/85 |
| 5,145,816 | 9/1992 | Beck et al. | 502/60 |
| 5,151,110 | 9/1992 | Bein et al. | 95/140 |
| 5,191,144 | 2/1993 | Le et al. | 585/643 |

OTHER PUBLICATIONS

Beck, J. S., et al., "A New Family of Mesoporous Molecular Sieves Prepared with Liquid Crystal Templates", Journal of the American Chemical Society, 114, No. 27, 10834–10843 (1992).

Kresge, C. T., et al., "Ordered mesoporous molecular sieves synthesized by a liquid-crystal template mechanism", Nature, vol. 359, 710–712 (1992).

Arnold, M. A., "Fiber-Optic Chemical Sensors", Analytical Chemistry, vol. 64, No. 21, 1015A–1025A (1992).

Walt, D. R., "Designing new sensors with old chemistry", Chemtech, 658–663 (1992).

Hughes, R. C., et al., "Chemical Microsensors", Science, vol 254, 74–80 (1991).

Lieberman, R. A., ed., "Chemical, Biochemical, and Environmental Fiber Sensors III", Proceedings International Society for Optical Engineering, vol. 1587; 67–73 (1991).

Bein, T., et al., "Molecular Sieve Sensors for Selective Detection at the Nanogram Level", Journal of the American Chemical Society, III, 7640–7641 (1989).

Demertzis, M., et al., "Potentials of Ion-exchanged Synthetic Zeolite-Polymer Membranes", J. Chem. Soc. Faraday Trans. 1, 82, 3647–3655 (1986).

(List continued on next page.)

Primary Examiner—Robert J. Warden
Assistant Examiner—L. M. Crawford
Attorney, Agent, or Firm—Alexander J. McKillop; Malcolm D. Keen; Dennis P. Santini

[57] ABSTRACT

A sensor device includes ultra-large pore crystalline material M41S as a selective detecting element, and a measuring element for quantifying physical, chemical or biological events which occur within the crystalline material. The crystalline material may also contain an additional selective detecting component within its pores.

43 Claims, 2 Drawing Sheets

OTHER PUBLICATIONS

Ozin, G. A., et al., "Advanced Zeolite Materials Science", Agnew. Chem. Ed. Engl., 28, No. 3, 359–376 (1989).

Ballantine, D. S., et al., "Surface Acoustic Wave Devices for Chemical Analysis", Analytical Chemistry, vol. 61, No. 11, 704A–714A (1989).

Li, Z., et al., "Self14 Assembling Trimolecular Redox Chains at Zeolite Y Modified Electrodes", Inorg. Chem, 28, 178–182 (1989).

Krueger, J. S. et al., "Long-Lived Light-Induces Charge Separation in a Zeolite L-Based Molecular Triad", J. Am. Chem. Soc. 110, 8232–8234 (1988).

Rose-Pehrsson, S. L., et al., "Detection of Hazardous Vapors Including Mixtures Using Pattern Recognition Analysis of Responses from Surface Acoustic Wave Devices", Anal. Chem. 60, 2801–2811 (1988).

Persaud, L., et al., "Photochemical Hydrogen Evolution via Singlet-State Electron-Transfer Quenching of Zinc Tetra (N-methyl-4-pyridyl)porphyrin Cations in a Zeolite L Based System", J. Am. Chem. Soc., 109, 7309–7314 (1987).

Li, Z., et al., "Vectorial Electron Transport at Ion-Exchanged Zeolite-Y-Modified Electrodes", J. Phys Chem., 91, 643–648 (1987).

SENSOR DEVICE CONTAINING MESOPOROUS CRYSTALLINE MATERIAL

BACKGROUND OF THE INVENTION

1. Field of the Invention

The invention relates to sensor devices which utilize in their structure a composition of matter comprising an inorganic, porous, non-layered crystalline phase material exhibiting, after calcination, an X-ray diffraction pattern with at least one peak at a d-spacing greater than about 18 Angstrom Units and having a benzene adsorption capacity of greater than 15 grams benzene per 100 grams of said material at 50 torr and 25° C.

2. Description of the Prior Art

Devices for the selective analysis of chemical and biochemical environments are used in testing, research, and chemical processing. Such devices are bio-, chemo- or electrosensors that can be used for single pass or continuous, in situ monitoring. Biosensors rely on biochemical interactions and can monitor biological systems for, e.g., temperature, pH, binding reactions and enzyme-catalyzed changes. Similarly, chemosensors rely on chemical interactions and can monitor chemical composition and concentration. Electrosensors can measure changes in current, impedance or potential.

A sensor device is generally composed of a selective element that responds to a change in the environment and a measuring element which detects the change yielding information which may be processed by a transducer into a readable form.

Measuring components are known in the art, and include, for example, piezoelectric, fiber optic, electrochemical autoradiographic, and spectrophotometric elements. These components have been used in sensors such as surface acoustic wave devices, fiber optic devices, electrochemical devices, devices utilizing spectroscopy or autoradiography and semiconductor devices.

SURFACE ACOUSTIC WAVE DEVICES

Surface acoustic wave (SAW) devices utilize a measuring system based on a piezoelectric crystal, the resonant frequency of which changes with changes in mass.

In surface acoustic wave devices, specially cut piezoelectric crystals can mechanically oscillate when subjected to an alternating electrical potential producing Rayleigh surface waves whose frequency changes with changes in mass. Interdigitial transducer electrodes, which can be photolithographically formed, are positioned on the surface of the piezoelectric crystal making it possible to excite and detect surface waves in the piezoelectric crystal. The electrodes are generally positioned on the same side of the crystal. A time-varying radio frequency (rf) voltage is applied and transducers convert the rf into a Rayleigh surface wave, i.e. deformations in the form of surface acoustic waves (SAW's) in the surface of the piezoelectric crystal. One set of electrodes causes the SAW's and another set acts as a receiver translating the wave to readable electrical signals.

A selective detecting layer may be placed on the piezoelectric crystal. A change in the detecting layer, e.g. absorption of a gas causes a change in mass thereby changing the resonant frequency of the piezoelectric crystal.

Piezoelectric crystals are commercially available and include ST-cut, X-propagating quartz which is temperature stable; Y-cut, Z propagating lithium niobate which has high piezoelectric coupling, and perovskite ($CaTiO_3$), also double oxide titanates of barium or lead, double oxide niobates of lithium and lead, and lead zirconia.

FIBER OPTIC SENSOR DEVICE

In a fiber optic device a central core is transparent to an involved light wavelength. The core is surrounded by an outer cladding which is a homogeneous dielectric capable of sustaining an electric field and having a lower refractive index than the central core. The cladding can be a detecting layer. Alternatively, an optical fiber may be used in a bifurcated arrangement with a distal tip or head having a detecting layer positioned upon it. Optical fibers are capable of conducting modulated light signals by total internal reflection.

When light passes along the core an evanescent electric field forms at the interface of the core and the cladding and also a short distance beyond the interface thereby exciting an indicator such as a fluorescent dye which may be positioned in a cladding detecting layer. A desired detected event such as an increase in pH, chemical changes or absorption of analyte in the detecting layer causes a change in the indicator such as a change in luminescence.

Optical fibers are generally ultra pure glass materials. Commercially available optical fibers include all-polymer fibers, silica fiber usually doped with germania, phosphorus pentoxide or boric oxide. Pure silica core fibers are especially useful for some fluorescence systems since they will propagate light in the near-violet. Other fiber materials include plastic-coated silica (PCS), glass and bundles of glass or polymer fibers grouped together.

The light sources for fiber optic measuring components are known in the art and include, for example, lasers, light emitting dioxides and white light sources, e.g., tungsten-halogen lamps. The desired wavelength may also be selected and focused using means known in the art such as optical filters and glass or quartz lenses. After passage through the fiber optic sensor, the light is collected, collimated and detected witch a solid-state diode or photo-multiplier tube and analyzed by a computer.

ELECTROCHEMICAL SENSING DEVICE

In an electrochemical device, the monitoring of chemical properties of a substance involves the measurement of redox changes or potential difference between two electrodes with the change or difference dependent on the chemical activity being measured.

In redox, oxidation or reduction occur as a result of electron transfer, and coupled chemical reactions. Coupled reactions are initiated by production or depletion of the primary products or reactants at an electrode surface. The physical or chemical phenomena in electrode sensing processes generally occur within a few micrometers of the electrode surface.

An example of an electrochemical sensing device is an ion selective electrode (ISE). An ISE can be connected with a detecting element which is usually a polymeric membrane containing a selective reagent such as a metal-specific ionophore or an enzyme. Alternatively, a glass electrode can be coated with the selective reagent such as an enzyme, antibody, or chemical reagent.

When a reaction takes place, a redox change or change in potential difference is measured.

SPECTROSCOPY

Spectrophotometric analyses can be used to detect qualitative and quantitative changes in a substrate film or solution and can be applied to gaseous, liquid or solid samples. An example is infrared spectroscopy (IR). Electromagnetic radiation of wavelengths between 1 and 300 μm (infrared) induces either rotational or vibrational energy level transitions within molecules being analyzed. The frequencies of infrared radiation absorbed by a molecule are determined by its rotational energy and by the force constants of the bonds in the molecule. The rotational energy and force constants are generally unique for each molecule so that the infrared spectrum of each molecule usually unique infrared spectrum fingerprints. For IR analysis, a thin film or solution may contain the analyte or a disk may be prepared by pressing an intimate mixture of the analyte with potassium bromide (KBr).

In addition to the qualitative determination of the presence of an analyte by its distinctive fingerprint, quantitative analysis may be undertaken based on the Bouguer-Lambert-Beer law as applied to a specific absorption band within the infrared spectrum of the analyte.

In general, spectrophotometric analysis can also be undertaken using the region of the electromagnetic spectrum between 200 nanometers and 300 micrometers. A source of radiation emits electromagnetic radiation which passes through a prism or grating dispersing the light so that a limited wavelength or frequency range is allowed to irradiate the sample. A detector such as a photocell measures the light transmitted by the sample.

AUTORADIOGRAPHY

Autoradiography is a photographic technique used to detect radiolabel. In solid phase radioimmunoassays, for example, one member of a binding pair, such as an antigen or antibody, is bound to a solid support, such as polyvinyl chloride or agarose gel. The opposite member of the bending pair is radiolabeled, e.g. with $^{125}$I and binding events are detected on autoradiograms.

SEMICONDUCTORS

Other known measuring components include semiconductor elements such as metal oxide semiconductor field-effect transistors (MOSFET), ion-sensitive field effect transistors (ISFET) and chemical sensitive filed effect transistor (CHEMFET). The gate metal in these may be adhered with or replaced with a sensor element which interacts with an analyte. Gate voltage is modulated by a sensed event and thus the event can be detected.

Sensing devices include a measuring element as described above and a selective element. Selective detecting components are often anchored to a permeable or impermeable substrate to form a selective element. For example, ion sensitive electrode devices have included substrates such as glass, resins or polymer membranes such as polyvinylchloride or polysaccharide to which sensing components such as ionophore molecules or enzymes are fixed. Sensing components have also been fixed to supports such as zeolites, resins, glass, ceramics and quartz, to interact with a specific chemical species to be measured using measuring components such as piezoelectric crystals and semiconductors.

The polymer membranes, zeolites, resins, glass, ceramics and quartz which have previously been used as substrates or supports in sensor devices differ in various ways from the ultra-large pore crystalline material used herein. The differences in microstructure of porous inorganic solids e.g. materials such as amorphous silica, layered materials and zeolites, or polymer membranes, glass, ceramics and quartz, result in important differences in the chemistry of these materials. Therefore, it is not possible to predicate a model for the use of the present ultra-large pore crystalline material in sensors based on the use of other porous or nonporous, inorganic or organic materials.

It is desirable that a substrate used as a support, host, container, carrier or package for sensor components be capable of anchoring the components and capable of contributing to the selectivity, accuracy, precision and rapid response of the sensor device. A desirable substrate is also durable, stable, inert and economical. Previously utilized substrates fail in one or more of these areas.

A sensor substrate which fulfills all these desirable attributes has now been conceived using the novel, synthetic, ultra-large pore crystalline material, M41S.

Accordingly, it is an object of the invention to provide sensing devices which include ultra-large pore crystalline material as stable, selective substrates or supports.

SUMMARY OF THE INVENTION

The present invention is a sensor device which includes an inorganic, porous, non-layered crystalline phase material which exhibits, after calcination, an X-ray diffraction pattern with at least one peak at a d-spacing greater than about 18 Angstrom Units with a relative intensity of 100 and has a benzene adsorption capacity of greater than 15 grams benzene per 100 grams of anhydrous crystal at 50 torr and 25° C. Selective components for determining physical or chemical changes are bonded or supported within the pores of the crystalline material.

In a preferred embodiment, the device includes an inorganic, porous, crystalline phase material having a hexagonal arrangement of uniformly-sized pores at least about 13 Angstroms in diameter and exhibiting, after calcination, a hexagonal electron diffraction pattern that can be indexed with a $d_{100}$ value greater than 18 Angstrom Units. Advantageously, the crystalline material can be tailored for the desired sensor selectivity because of its flexible ability to be functionalized in many different ways.

DETAILED DESCRIPTION OF THE INVENTION

Figure 1:
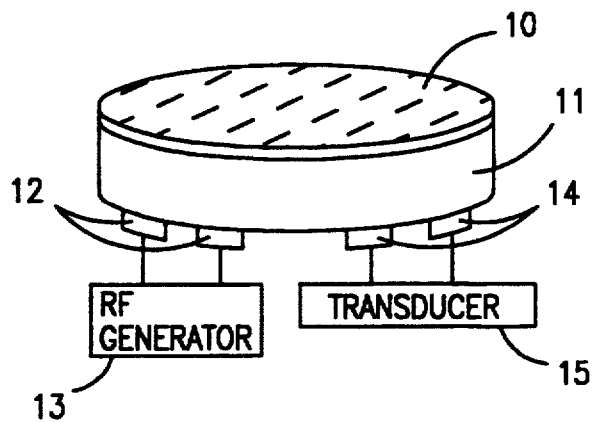
FIG. 1 is a schematic diagram of a surface acoustic wave device.

The sensor devices contemplated herein include a mesoporous crystalline phase material as a component.

The composition of the mesoporous crystalline material is described in U.S. Pat. Nos. 5,102,643 and 5,098,684; and the synthesis of the material is described in U.S. Pat. Nos. 5,108,725 and 5,057,296, the entire disclosures of which are herein incorporated by reference in their entireties. The functionalization of the material is described in U.S. Pat. No. 5,145,816 which is herein incorporated by reference in its entirety.

The inorganic, porous, non-layered crystalline phase material, which exhibits, after calcination, an X-ray diffraction pattern with at least one peak at a d-spacing greater than about 18 Angstrom Units with a relative intensity of 100 and has a benzene adsorption capacity of greater than 15 grams benzene per 100 grams of anhydrous crystal at 50 torr and 25° C., has been termed M41S.

The inorganic, porous, crystalline phase material, having a hexagonal arrangement of uniformly-sized pores at least about 13 Angstroms in diameter and exhibiting, after calcination, a hexagonal electron diffraction pattern that can be indexed with a $d_{100}$ value greater than 18 Angstrom units, is included within the class of crystalline materials termed M41S and has been termed MCM-41.

M41S molecular sieves are unique mesoporous materials that offer high surface area, a uniform pore system, high sorption capacity, and a stable structure. The chemical composition of the pore wall interior can be varied to modify the chemical adsorption and chemical function of the pores. Furthermore, M41S materials have unusually large pores capable of supporting sensing components. These materials also contain a high silanol content within the pores which allows functionalization of the pore walls to impart size selective and chemical selective characteristics to the molecular sieve. M41S materials offer unique selectivity for specific compounds due to the uniform pore size that can be prepared from 15 Å to greater than 100 Å. The silica based composition of M41S materials offers a stable and inert porous material for the sensor under most conditions. The high surface area and sorption capacity of M41S materials allows increased sensitivity.

For this application M41S material can be used in various forms: as synthesized, low temperature (<150° C.) organic extracted, and high temperature (>300° C.) organic extracted, for example, by calcination. After crystallization, as-synthesized M41S materials retain the surfactant template system within the pore structure. The surfactant template system may contain only the surfactant molecules or it may also contain any additional auxiliary organics used in the preparation of the M41S. The presence of these organic molecules within the pore structure provides a more hydrophobic environment than that of similar non-functionalized M41S materials without the template system. The as-synthesized M41S materials may enhance the adsorption affinity of the desired molecule used in the sensor.

Low temperature organic extracted M41S materials are those whose surfactant system has been partially or completely removed by some extraction or ion exchange method so that the pore system is either completely or partially free of any organic molecules that were present in the as-synthesized material. These low temperature organic extracted materials contain a high number of silanol groups within the pore structure that could function as anchors for the desired functionalization of the M41S sensor. The number of silanol groups is higher than in similar M41S materials which have had the organic extracted by oxidative methods or high temperature methods (see calcined M41S). The pore system of the organic extracted M41S materials can be expected to be less hydrophobic and have more polar character than that of the as-synthesized materials.

Calcined or high temperature organic extracted M41S materials have had the surfactant template system removed by oxidative treatment usually at temperatures >300° C. in an oxidizing atmosphere (e.g., air). The number of silanol groups remaining within the pore system is a function of the time and temperature of this treatment. However, the number can be expected to be less than that of the low temperature organic extracted M41S. Dehydroxylation, which is favored at higher temperatures, is the mechanism for reducing the number of silanol groups. A reduced number of silanol groups represents a lower number and different spacing of the anchors used for the functionalization of the M41S sensor. The pore system of the calcined material may be more hydrophobic than that of the organic extracted M41S materials. M41S materials in which the organic has been extracted can be easily functionalized for the desired process.

A method for extracting organics from M41S is described in U.S. Pat. No. 5,143,879, herein incorporated by reference.

The sensor device contemplated herein utilizes M41S as a substrate which acts as a support, host, container, carrier or package for selective components bonded or supported, e.g. covalently bonded, coordinatively attached, hydrogen bonded, or simply present within its pores. The pore size of the molecular sieve material may be adjusted for the selective absorption of a particular molecule either by using the appropriate template during synthesis, as described in U.S. Pat. Nos. 5,108,725 and 5,057,296, or by chemical molecular engineering of the pore walls as described, for example, in U.S. Pat. No. 5,148,816. For example, the pores may be functionalized with a chemically active component which will react with and thereby sense the presence of molecules which are being monitored. Absorption or chemical reactions are then detected and quantified by a measuring component.

Therefore, sensor devices of the invention include a selective detecting element that responds to a change in the environment and a measuring element which processes the signal. The detections are carried out using a mesoporous molecular sieve which supports a selective detecting component. In the sensors of the invention, the crystalline material can act as a shape selective, charge selective and size selective substrate to impart a chemically specific environment for absorbed molecules. The devices of the invention are capable of a temperature sensitivity from sub ambient up to about 100° C.

When used in a Surface Acoustic Wave device, the mesoporous crystalline material is coated on the surface of a piezoelectric crystal using dip coating methods or press coating methods known in the art. The thickness of the coating is from about 0.02 micron to about 50 microns, preferably from about 0.1 micron to about 2 microns. The piezoelectric crystal is a quartz resonator whose resonant frequency changes, e.g., with changes in mass. The mesoporous crystalline material may be functionalized for the desired detection. For example, the pore size can be adjusted for sorption of or reaction with a gas such as pyridine, thiophenes, mercaptans, furans, aromatics (benzene, etc.), methane, carbon dioxide, carbon monoxide, $NO_x$, $SO_x$.

A target analyte (gas) can be sorbed, reacted with, or otherwise trapped within the coating producing a change in the mass of the coating thereby perturbing the SAW's. The perturbation is detected electronically as a shift in the frequency of the oscillator circuit. The sensitivity and selectivity of the SAW device depends on the properties of the M41S coating. These SAW devices may be used to detect gases at sub-parts-per-million.

FIG. 1 shows a Surface Acoustic Wave device (not to scale). Functionalized M41S material 10 is coated on a piezoelectric crystal 11 and electrodes 12 are used to apply a time-varying radio frequency with rf generator 13 while other electrodes 14 connected to a transducer means 15 act as a receiver translating the SAW's to readable electrical signals. An analyte/coating interaction produces a change in the properties of the coating, e.g., density, mass, viscosity modulus, dielectric constant, and thus alters the amplitude or velocity of the surface acoustic wave of the quartz resonator. The sensitivity and selectivity of the SAW sensor is thus a function of the physicochemical properties of the M41S.

In a Fiber Optic Sensor, the analyte being detected changes the features of light transmitted along the fiber and these changes modify an electrical signal in a receiver. Fluorescent or dye molecules may be used as indicators. In order to use fluorescence in an optical fiber sensor, the spectral characteristics of the light source, dye and detector system must be matched. Light source and detector will typically be broadband devices which have been restricted to operate over a more narrow wavelength range by the addition of lenses.

In an optical fiber, an evanescent field which forms around the fiber core when light passes through is a superposition of the field distributions of all the modes propagating within the fiber. An important use of the evanescent field is the excitation of fluorescence. If a fluorescent molecule is within the evanescent field region, as long as the wavelength of the radiation is matched to the absorption spectrum of the fluorophore, the molecule will be elevated to an excited state.

Figure 2:
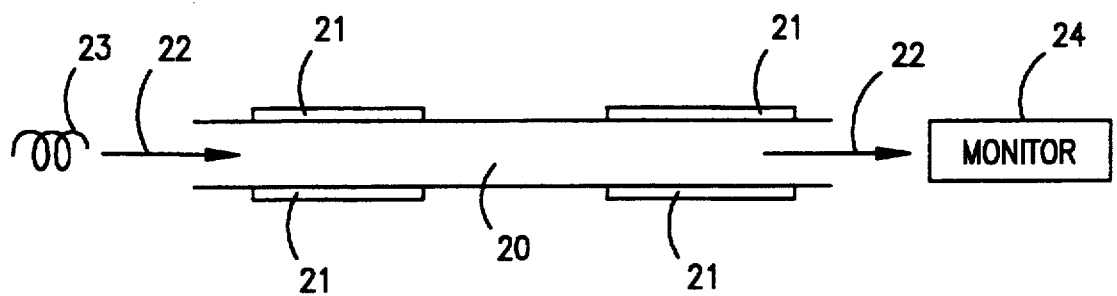
FIG. 2 is a schematic diagram of a fiber optic device.

When used in a fiber optic sensing device, an analyte such as $NH_3$, HCN, $CO_2$, CO, $SO_2$, $NO_x$, $O_2$, $H_2O_2$, organoamines, thiophenes, nitrogen containing ring compounds such as pyridine, piperdine, and pyrrolidine, heavy metal ions such as K and Zn and protonic acids and an indicator molecule such as rhodamine 6G, rhodamine B, naphthazin, quinidines, coumarines, ruthenium complexes, nile blue, malachite green, crystal violet, fluorescein, resorufin, cresyl violet, methylembelli ferone, carbonic anhydrase and oxazines are functionalized into M41S material along with an analyte. As shown in FIG. 2 (not to scale), a fiber optic cable 20 having a thickness of 50 to 500 microns, is coated with the M41S material in a thickness of about 0.1 microns to about 50 microns as a cladding 21 arranged as two segments for a length of from about 50 microns to about 1000 microns, preferably 100 to 500 microns along the fiber optic cable which is the core. Light 22 is pumped through the cable from a light source 23 and luminescence caused by evanescence in the cladding interface is detected by a monitor means 24.

This evanescent field configuration is advantageous, for example, in monitoring the binding of ligands to antibody immobilized in the M41S. Such antibodies may have dimensions of about 10 nm.

Figure 3:
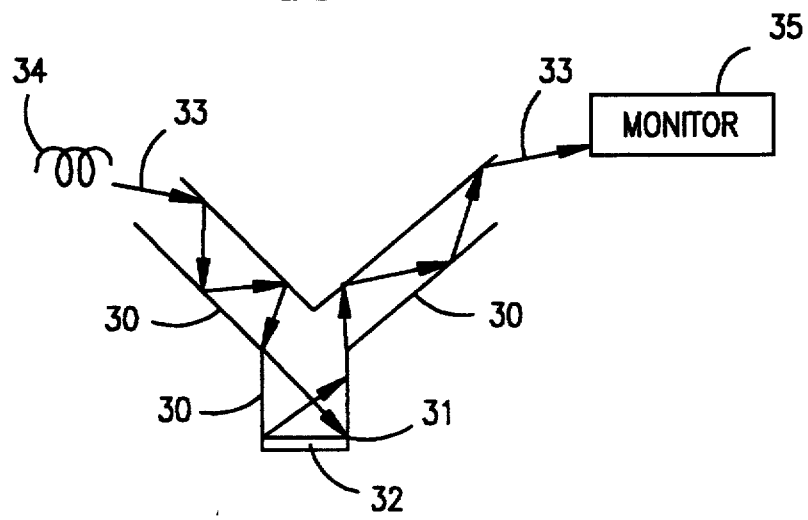
FIG. 3 is a schematic diagram of a bifurcated fiber optic device.

A bifurcated optical fiber sensing device is shown in FIG. 3 (not to scale). A bifurcated optical fiber 30 as in FIG. 2 is bifurcated to have a bifurcation head. The cable is coated at the bifurcation head 31 with functionalized M41S containing analyte and indicator molecule 32 in a coating thickness of about 50 microns to about 1000 microns, preferably about 100 to about 500 microns. Light 33 is pumped through the cable from a light source 34 and change in luminescence caused by analyte reaction is detected by monitor means 35. An advantage of the bifurcated arrangement is that the light source and detector can be connected to a common sensor region without need for ancillary optics. The intensity or lifetime of the fluorescence depends on the presence of the analyte.

In a fiber optic sensor, the M41S may be the support for enzymes or a member of a binding pair such as antigens or antibodies and used to detect the enzyme substrate or opposite member of the binding pair.

The fiber optic device may also be used to detect pH using a fluorescent pH indicator dye such as those listed in Table 1 below. Changes in the dye's absorbance or fluorescence correlates with pH changes and is reversible.

TABLE 1

| pH ranges | |
|---|---|
| 9.5–10 | Quinine (2nd endpoint) |
| 9.0–11 | Ethoxyphenylnaphthastilbazonium chloride |
| 8.4–10.4 | Acridine Orange |
| 8.6–10 | $\beta$-Naphthol |
| 8.2–10 | Naphthazol derivatives |
| 6.5–7.6 | Umbelliferone |
| 6.5–7.5 | Brilliant Diazol Yellow |
| 6.5–7 | Thioflavine |
| 5.8–8.2 | 3,6-Dioxythalic dinitrile |
| 5.4–7.6 | 3,6-Dioxyxanthone |
| 5.0–6.1 | Quinine (1st endpoint) |
| 4.9–5.1 | Acridine |
| 4.4–6.4 | Resorufin |
| 4.0–4.5 | Erythrosine |
| 4.0–4.5 | Fluorescein |
| 3.4–5.0 | Phloxine |
| 3.4–4.8 | $\alpha$-Naphthylamine |

The M41S may also be used in an electrochemical sensor. Biological or chemical analytes may be ionophorically immobilized on, e.g., impregnated into, a membrane electrode such as a polymer which includes the crystalline material as a support for an ionophore thus forming an ion selective electrode (ISE). Ionophores with known ionic selectivities include porphyrins and organic square planar molecules such as cyclams, salens and cryptands. An ion selective electrode can be used for determining the amount of free analyte or metal ions in a sample. The term ISE is generally applied to a membrane electrode which responds selectively toward a free analyte or an ion species in the presence of other ions in a liquid or gas. The selectivity of the electrode depends primarily on the selectivity of the ion-exchange process with the ionophore. For use in an electrochemical sensing system, M41S material may be functionalized with an ion-selective ionophore molecule such as phenanthroline, porphyrins, salens, salophens, cryptands, cyclams, crown ethers, etc. and/or with an analyte, enzyme, antibody or antigen. The functionalized M41S can be immobilized in a polymeric membrane or coated on a glass electrode.

When an analyte is affixed to the crystalline material in a membrane electrode, the reaction between analytes, for example an antibody and an antigen, produces a potential change which can be monitored with potentiometric electrodes by means known in the art. The quantity of specific material selected for is transformed into a detectable signal by a transducer.

An advantage of using M41S material in an electrochemical sensor is that covalent attachment of a sample to the M41S positions the sample so that it will not be dislodged during liquid-phase chemistry.

Fixed analytes which can be immobilized on the mesoporous crystalline material in an ISE include the immobilized analytes listed in Table 2 below.

Ion selective membranes containing the functionalized M41S can be made by embedding the functionalized M41S in a plastic material such a low viscosity epoxide resin monomer system followed by polymerization. Polyvinyl chloride or cellulose acetate are also useful materials for the membrane. The following electrode system can be used.

electrode |internal solution ||external solution |electrode
membrane

The membrane preferably includes a plasticizer.

Figure 4:
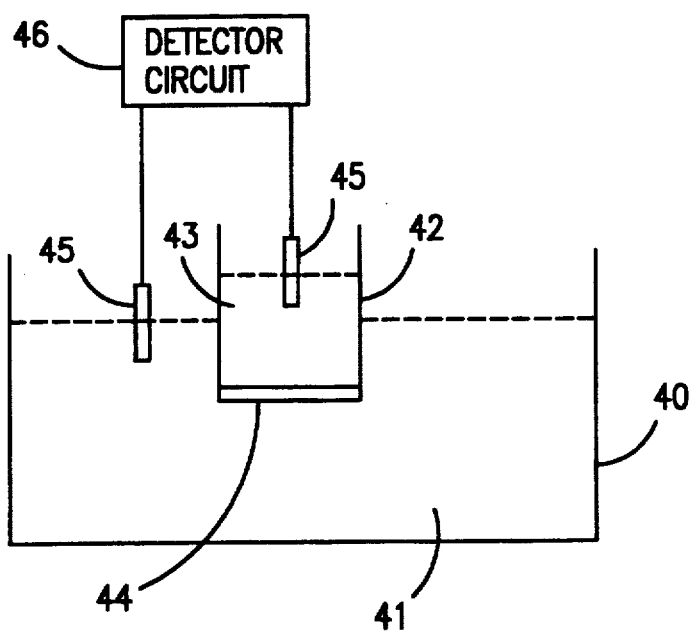
FIG. 4 is a schematic diagram of an electrochemical device.

An electrochemical sensor is shown in FIG. 4. A first container 40 holds an external analyte solution 41 such as a solution containing antigen or antibody. A second container 42 holds an internal solution 43 containing metal ions. An ion sensitive electrode 44 consists of a polymeric membrane containing embedded crystals of M41S material which has been functionalized with an ionophore coupled with antigen or antibody which is expected to bind to the analyte in the external solution 41. Reaction of antigen with antibody modulates the ion carrier potential of the ionophore and produces a potential change detected by reference electrodes 45 connected to a detecting means 46. The M41S is capable of holding the ionophore and analyte more securely than polymers alone. The M41S may be used as a support for analytes in a detection of an enzymatic reaction or a selective binding reaction. Some binding pairs are illustrated in Table 2.

TABLE 2

| Affinity Systems Analytes Which Can Be Supported by the Substrate and Which Bind to Each Other | |
|---|---|
| antigen | antibody |
| hapten | antibody |
| polysaccharides; monosaccharides | lectin; receptors |
| glycoproteins | lectin; receptors |
| glycolipids | lectin |
| enzyme | enzyme; substrate; cofactor |
| enzyme inhibitor | enzyme |
| neurotransmitters | neural receptor |
| hormones | neural receptor |
| nucleic acid, single strand | nucleic acid, complementary strand |

In bio-sensors, either biological analyte in each pair is affixed to the ultra-large pore crystalline substrate of the invention by covalent binding to silanols in the crystalline material using chemical methods known in the art, such as those described by E. Harlow and D. Lane, "Antibodies, A Laboratory Manual", Cold Spring Harbor Laboratory 1988. Bridge molecules such as multifunctional aldehydes (glutaraldehyde), or silanes can be used to attach the analyte. The interaction between the affixed analyte and a test sample is monitored, e.g., by competitive assay. The measuring means can utilize, for example, electrochemical, fiber optic or autoradiographic measuring components, e.g. fluorescence or detection of radiolabel such as $^{125}I$, $^3H$, or $^{35}S$ - labeled methionine or cysteine (for proteins). Enzymes include deaminases, e.g. urease, decarboxylase, ester bond hydrolases, e.g. acetylcholinesterase, and dehydrogenases, e.g. glutamate dehydrogenase.

In one type of sensing system, an enzyme is allowed to oxidize its substrate, e.g. glucose oxidase and glucose, releasing electrons that are captured by other molecules known as electron transfer agents. Electron transfer agents then transfer the signal, as a function of concentration of the analyte, to an electrosensoring device. Electron transfer agents including, e.g., methyl viologen, bipyridinium complexes, ferrocene molecules and metal porphyrins which can be affixed to the M41S material. Biosensors can also utilize enzyme thermistors and enzyme transistors.

The M41S material may also be used as a support for analytes in sensors utilizing spectroscopic analysis. As an example for use with spectroscopy as the measuring means, the M41S material may be functionalized with Lewis base sites such as with nitrogen-containing polymers, e.g. polypyrrole or amines, the material is used to detect a Lewis acid such as $BF_3$. Likewise, when functionalized with Lewis acid sites, such as with added aluminum, copper, cobalt or transition metals, the material is used to detect a Lewis base such as nitrogen compounds, e.g. ammonia, phosphines, arsines, NO, HCN, sulfur compounds such as $SO_x$ and sulfides, and carbon compounds such as CO and $CO_2$.

The M41S can be functionalized for example, by contacting crystalline material with diethylaluminium chloride to functionalize Si-OH sites as follows:

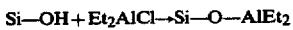

Et=ethyl

This site has an open orbital which can combine with ammonia. The M41S can likewise be functionalized with a tricoordinate amine, for example, as follows:

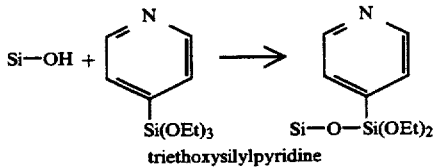

This material can be used to detect Lewis acids such as $BF_3$, $H_2O$ and alkyl aluminum. In other embodiments, a polymer containing Lewis acid or Lewis base, e.g. polyaniline or polypyrrole, may be supported in unbonded condition within the pores of the mesoporous crystalline material and used to detect gases.

The M41S can also serve as a framework for intracrystalline electrode components with the incorporation metal clusters, metal oxides, organometallic or organic components polypyrrole which act as nanoelectrodes. For this purpose, encapsulated clusters of platinum or ruthenium or osmium tris(bipyridyl) metal complexes may act as microelectrodes. Persaud et al., *Inorg. Chem.* 26, 3825 (1987) describe a method for platinum deposition.

FUNCTIONALIZATION OF CRYSTALLINE MATERIAL

The new class of molecular sieves to be used in the invention has a unique property wherein a high concentration of hydroxyl groups may be present within the pore openings of the as-synthesized or calcined material. The reaction of these groups, wherein organics from the synthesis mixture may remain, with a treatment compound comprising M'X'Y'$_n$ can anchor or incorporate functional groups into the molecular sieve material. The functional groups can provide unique chemically reactive sites within the pores or can act as pore size reducing agents so that the pore size can be tailored as desired.

A functional group will be understood to be a characteristic reactive, covalently bonded, coordinatively attached or hydrogen bonded group of a chemical compound and functionalization will be understood to be the incorporation of functional groups into the molecular sieve material.

When the group is covalently bonded, the functionalization reaction may be described, for example, according to the formula Si—O—R' + M'X'Y'$_N$ → SiOM'Y'$_N$ + R'X' wherein Si—O—R' is a site in the lattice of the crystalline material.

R' = H+ or R$_4$N+ which is the organic cation specified in the crystallization methods described hereinbelow.

M' = Elements of Groups IIA, IIIA, IVA, VA, VIA, VIIIA, IB, IIB, IIIB, IVB, VB, or VIB of the Periodic Table of the Elements, (Sargent-Welch Scientific Co. Cat. No. S-18806, 1979). Preferred elements for M' are Groups IVA, VIA, VIIIA, IIIB and IVB, and most preferred elements for M' are titanium, chromium, iron, cobalt, nickel, boron, aluminum and silicon.

X' = halides, hydrides, alkoxides of 1–6 carbon atoms, alkyl of 1–18 carbon atoms, alkenyl of C$_{1-18}$, aryl of 1–18 carbon atoms, acetates, aryloxides of 1–18 carbon atoms, sulfonates and nitrates. Preferred substituents for X' are halides, alkoxides of 1–6 carbon atoms and acetates. Most preferred substituents for X' are halides, alkoxides of 1–6 carbon atoms and acetates.

Y' can be selected from the substituents described for X', or amines, phosphines, sulfides, carbonyls and cyanos. Preferred substituents for Y' are those described for X', amines, sulfides and alkyls with 1–18 carbon atoms. Most preferred substituents for Y' are those described for X', amines and alkyls with 1–18 carbon atoms; n = 1–5.

Nonlimiting examples for M'X'Y'$_n$ include chromium acetate, chromium nitrate, tetraethylorthosilicate, tetramethylorthosilicate, titanium tetraethoxide, aluminum isopropoxide, aluminum tri-sec butoxide, hexamethyldisilazane, di-sec-butoxyaluminoxytriethoxysilane, diethylphosphatoethyltriethyoxysilane, trimethylborate, chlorodimethylalkylsilane wherein alkyl has 1–18 carbon atoms, ammonia-borane, borane-tetrahydrofuran and dimethylsulfidedibromoborane.

The ratio of treatment composition to treated composition of matter, duration of treatment and temperature are not critical and may vary within wide limits. The temperature may be, for example, from about −70° C. to about 250° C., with from about 25° C. to about 100° C. preferred; and the time may be from about 0.1 to about 100 hours, with from about 0.1 to about 30 hours preferred and from about 0.1 to about 24 hours most preferred.

The treated crystalline material can be used as is or may be further subjected to a thermal treatment or treatment with a reactive gas such as oxygen or carbon monoxide for activation. The treated material may be calcined in a reactive or inert gas such as NH$_3$, PH$_3$, air, O$_2$, N$_2$, Ar, SiH$_4$, H$_2$ or B$_2$H$_6$.

The treated crystalline material may be described as having functional groups within it according to the formula

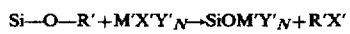

These functionalized sites may be, for example:

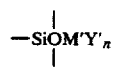

—SiOB(OMe)$_2$, —SiOB(Br)$_2$.SMe$_2$, —SiOTi(OEt)$_3$, —SiOCr(acetate)$_2$, SiOCr(nitrate)$_2$, —SiOSi(OMe)$_3$, —SiOAl(s—OPr)$_2$, —SiOAl(s—OBu)$_2$, —SiOSi(OEt)$_3$,

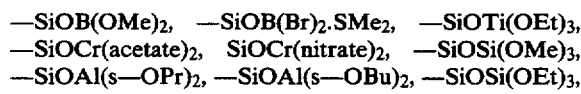

—SiOSi(CH$_3$)$_3$, —SiOSi(CH$_3$)$_2$C$_6$H$_{13}$, —SiOSi(CH$_3$)$_2$C$_{18}$H$_{37}$, —SiOSi(CH$_3$)$_2$C$_6$H$_5$; Me = CH$_3$, Et = C$_2$H$_5$, Pr = C$^3$H$_7$, Bu = C$_4$H$_9$.

In these examples, —Si represents a site in the lattice of the crystalline material. Two additional bonds on the Si are not shown. The invention is not limited to these listed functionalized sites.

Chemical sensor devices using the crystalline material can be functionalized for use in a hydrophilic or hydrophobic operation such as in a detecting system for groundwater monitoring. The crystalline material may be rendered hydrophobic by functionalization with silicon-containing compounds such as silanes and silazanes. The crystalline material may be rendered hydrophilic by a change in wall composition and/or functionalization with a molecular entity containing a polar or charged group for example, anionic surfactant moieties including, e.g., phosphates, —(PO$_3$)$^{2-}$, sulfates, sulfonates or sulfoxides, —(SO$_3$)$^{1-}$, —CH$_2$—[SO]—CH$_3$, or carboxylates, —(CO$_2$)$^{1-}$. These surfactant moieties may be introduced in a form which includes counterions such as sodium, potassium and ammonium and an alkyl, aryl or alkylaryl substituents modified with double bonds or ester or amide groups in the hydrocarbon or as substituents themselves. With M41S functionalized in this way, detection devices can be used for monitoring water content in arid soils, e.g. to signal irrigation needs, and water content in cement or other porous construction media use for structures such as dams, etc.

Sensors which include M41S as a component can also be used in detection for gas purity for specialty gas distribution systems. Trace levels of hydrocarbon contaminants or water present in specialty gases such as $CO_2$ can be absorbed by the mesoporous material and detected. The crystalline material may be functionalized with a hydrophilic moiety as described above to detect water and the pore size may also be adjusted to sorb hydrocarbons while allowing the smaller molecules of carbon dioxide to flow through.

Similarly, in the electronic manufacturing of semiconductors, chemical vapor deposition of organometallic, organosilicate and liquant dopant materials is carried out using a carrier, e.g., nitrogen gas, silanes, hydrogen chloride, phosphine, or arsine, from which moisture, oxygen and metal contaminants must be removed. The sensors of the invention, utilizing the extraordinarily large surface area of M41S are capable of a sensitivity sufficiently acute to monitor contaminants at very low levels, for example using electron capture of the contaminants as they become adsorbed to the crystalline substrate. Water can be detected with a hydrophilic function as described above. Metal contaminants can be detected with chelating agents supported in the crystalline material.

CRYSTALLINE MATERIAL

As demonstrated hereinafter, the inorganic, non-layered mesoporous crystalline material of this invention has the following composition:

$$M_{n/q}(W_aX_bY_cZ_dO_h)$$

wherein W is a divalent element, such as a divalent first row transition metal, e.g. manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c and d are mole fractions of W, X, Y and Z, respectively; h is a number of from 1 to 2.5; and $(a+b+c+d)=1$.

A preferred embodiment of the above crystalline material is when $(a+b+c)$ is greater than d, and $h=2$. A further embodiment is when a and $d=0$, and $h=2$.

In the as-synthesized form, the material of this invention has a composition, on an anhydrous basis, expressed empirically as follows:

$$rRM_{n/q}(W_aX_bY_cZ_dO_h)$$

wherein R is the total organic material not included in M as an ion, and r is the coefficient for R, i.e. the number of moles or mole fraction of R.

The M and R components are associated with the material as a result of their presence during crystallization, and are easily removed or, in the case of M, replaced by post-crystallization methods hereinafter more particularly described.

To the extent desired, the original M, e.g. sodium ions of the as-synthesized material of this invention can be replaced in accordance with techniques well known in the art, at least in part, by ion exchange with other ions. Preferred replacement ions include metal ions, hydrogen ions, hydrogen precursor, e.g. ammonium, ions and mixtures thereof. Particularly preferred ions are those which tailor the catalytic activity for certain hydrocarbon conversion reactions. These include hydrogen, rare earth metals and metals of Group IA (e.g. K), IIA (e.g. Ca), VIIA (e.g. Mn), VIIIA (e.g. Ni), IB (e.g. Cu), IIB (e.g. Zn), IIIB (e.g. In), IVB (e.g. Sn), and VIIB (e.g. F) of the Periodic Table of the Elements (Sargent-Welch Scientific Co. Cat. No. S18806, 1979) and mixtures thereof.

The crystalline (i.e. meant here as having sufficient order to provide a diffraction pattern such as, for example, by X-ray, electron or neutron diffraction, following calcination with at least one peak) mesoporous material of this invention may be characterized by its heretofore unknown structure, including extremely large pore windows, and high sorption capacity. The term "mesoporous" is used here to indicate crystals having uniform pores within the range of at least about 13 Angstroms or from about 13 Angstroms to about 200 Angstroms. The materials of this invention will have uniform pores within the range of from about 13 Angstroms to about 200 Angstroms, more usually from about 15 Angstroms to about 100 Angstroms. For the purposes of this application, a working definition of "porous" is a material that adsorbs at least 1 gram of a small molecule, such as Ar, $N_2$, n-hexane or cyclohexane, per 100 grams of the solid.

The material of the present invention can be distinguished from other porous inorganic solids by the regularity of its large open pores, whose pore size more nearly resembles that of amorphous or paracrystalline materials, but whose regular arrangement and uniformity of size (pore size distribution within a single phase of, for example, ±25%, usually ±15% or less of the average pore size of that phase) resemble more those of crystalline framework materials such as zeolites. In one form the material appears to have a hexagonal arrangement of large channels that can be synthesized with open internal diameters from about 13 Angstroms to about 200 Angstroms. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as ±25% random deviation from the average repeat distance between adjacent channels still clearly give recognizable images of the present ultra-large pore materials. Comparable variations are also observed in the $d_{100}$ values from the electron diffraction patterns.

Some of these preparations of the material of the present invention give an X-ray diffraction pattern with a few distinct maxima in the extreme low angle region. The positions of these peaks approximately fit the positions of the hk0 reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material in them. Other techniques to illustrate the microstructure of this material are transmission electron microscopy and electron diffraction. Properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hkO projection of the hexagonal lattice and is related to the repeat distance $a_0$ between channels observed in the electron micrographs through the formula $d_{100}=a_0\sqrt{3}/2$. This $d_{100}$ spacing observed in the electron diffraction patterns corresponds to the d-spacing of a low angle peak in the X-ray diffraction pattern of the material. The most highly ordered preparations of the material obtained so far have 20–40 distinct spots observable in the electron diffraction patterns. These patterns can be indexed with the hexagonal hkO subset of unique reflections of 100, 110, 200, 210, etc., and their symmetry-related reflections.

In its calcined form, the crystalline material of the invention may be further characterized by an X-ray diffraction pattern with at least one peak at a position greater than about 18 Angstrom Units d-spacing (4.909 degrees two-theta for Cu K-alpha radiation) which corresponds to the $d_{100}$ value of the electron diffraction pattern of the material, and an equilibrium. benzene adsorption capacity of greater than about 15 grams benzene/100 grams crystal at 50 torr and 25° C. This sorption is based on the assumption that the crystal material has been treated if necessary in an attempt to insure no pore blockage by incidental contaminants.

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g. thermal treatment. Pore blocking inorganic amorphous materials silica, and organics may be removed by contact with acid or base or other chemical agents such that the detrital material will be removed without detrimental effect on the crystal of the invention.

More particularly, the calcined crystalline non-layered material of the invention may be characterized by an X-ray diffraction pattern with at least two peaks at positions greater than about 10 Angstrom Units d-spacing (8.842 degrees two-theta for Cu K-alpha radiation), at least one of which is at a position greater than about 18 Angstrom Units d-spacing, and no peaks at positions less than about 10 Angstrom units d-spacing with relative intensity greater than about 20% of the strongest peak. Still more particularly, the X-ray diffraction pattern of the calcined material of this invention will have no peaks at positions less than about 10 Angstrom units d-spacing with relative intensity greater than about 10% of the strongest peak. In any event, at least one peak in the X-ray diffraction pattern will have a d-spacing that corresponds to the $d_{100}$ value of the electron diffraction pattern of the material.

Still more particularly, the calcined inorganic, non-layered crystalline material of the invention is characterized as having a pore size of about 13 Angstroms or greater as measured by physisorption measurements, hereinafter more particularly set forth. Pore size is considered a maximum perpendicular cross-section pore dimension of the crystal.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The materials of the present invention that have the largest pore sizes may require more highly collimated incident X-ray beams in order to resolve the low angle peak from the transmitted incident X-ray beam.

The diffraction data were recorded by step-scanning at 0.04 degrees of two-theta, where theta is the Bragg angle, and a counting time of 10 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75–100), s=strong (50–74), m=medium (25–49) and w=weak (0–24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change: in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity is determined by contacting the material of the invention, after dehydration or calcination at, for example, about 450° C.–700° C. or about 540° C. for at least about one hour and other treatment, if necessary, in an attempt to remove any pore blocking contaminants, at 25° C. and 50 torr benzene until equilibrium is reached. The weight of benzene sorbed is then determined as more particularly described hereinafter.

The composition of the invention can be subjected to treatment to remove part or all of any organic constituent. The organic constituent can be removed by calcination or by solvent extraction as described in U.S. Pat. No. 5,143,879 to Whitehurst which is herein incorporated by reference in its entirety.

Components such as tungsten, vanadium, molybdenum, rhenium, nickel, cobalt, chromium, manganese, or a noble metal such as platinum or palladium or mixtures thereof can be in the composition by way of co-crystallization, exchanged into the composition to the extent a Group IIIB element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline material, especially in its metal, hydrogen and ammonium forms can be beneficially converted to another form by thermal treatment (calcination). This thermal treatment is generally performed by heating one of these forms at a temperature of at least 370° C. or 400° C. for at least 1 minute and generally not longer than 20 hours, preferably from about 1 to about 10 hours. While subatmospheric pressure can be employed for the thermal treatment, atmospheric pressure is desired for reasons of convenience, such as in air, nitrogens, ammonia, etc.

The crystalline material can be dehydrated, at least partially. This can be done by heating to a temperature in the range of 200° C. to 600° C. in an atmosphere such as air, nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

SYNTHESIS OF CRYSTALLINE MATERIAL

The usual method for synthesis of the ultra-large pore crystalline material involves preparation of a particular reaction mixture comprising sources of alkali or alkaline earth metal cation, if desired, one or a combination of oxides selected from the group consisting of divalent element, trivalent element, tetravalent element and pentavalent element, an organic directing agent and solvent or solvent mixture, maintaining said mixture under sufficient conditions of pH, temperature and time for formation of said composition of matter, and recovering said composition of matter. In this usual method, the organic directing agent is an ion of the formula $R_1R_2R_3R_4Q^+$, wherein Q is nitrogen or phosphorus and wherein at least one of $R_1$, $R_2$, $R_3$ and $R_4$ is aryl or alkyl of from 6 to about 36 carbon atoms or combinations thereof, the remainder of $R_1$, $R_2$, $R_3$ and $R_4$ being selected from the group consisting of hydrogen, alkyl of from 1 to 5 carbon atoms and combinations thereof. The compound from which the above organic directing agent ammonium or phosphonium ion is derived may be, for example, the hydroxide, halide, silicate or mixture thereof. The solvent or solvent mixture for use in the usual method comprises a $C_1$–$C_6$ alcohol, $C_1$–$C_6$ diol, water or mixture thereof, with water preferred.

A first method involves a reaction mixture having an $X_2O_3$/$YO_2$ mole ratio of from 0 to about 0.5, but an $Al_2O_3$/$SiO_2$ mole ratio of from 0 to 0.01, a crystallization temperature of from about 25° C. to about 250° C., preferably from about 50° C. to about 175° C., and an organic directing agent, hereinafter more particularly described, or, preferably a combination of that organic directing agent plus an additional organic directing agent, hereinafter more particularly described. This first method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, an organic (R) directing agent, hereinafter more particularly described, and a solvent or solvent mixture, such as, for example, $C_1$–$C_6$ alcohols, $C_1$–$C_6$ diols and/or water, especially water, said reaction mixture having a composition, in terms of mole ratios of oxides, within the following ranges:

| Reactants | Useful | Preferred |
|---|---|---|
| $X_2O_3$/$YO_2$ | 0 to 0.5 | 0.001 to 0.5 |
| $Al_2O_3$/$SiO_2$ | 0 to 0.01 | 0.001 to 0.01 |
| $X_2O_3$/($YO_2$ + $Z_2O_5$) | 0.1 to 100 | 0.1 to 20 |
| $X_2O_3$/($YO_2$ + WO + $Z_2O_5$) | 0.1 to 100 | 0.1 to 20 |
| Solvent/ ($YO_2$ + WO + $Z_2O_5$ + $X_2O_3$) | 1 to 1500 | 5 to 1000 |
| $OH^-$/$YO_2$ | 0 to 10 | 0 to 5 |
| ($M_{2/e}O$ + $R_{2/f}O$)/ ($YO_2$ + WO + $Z_2O_5$ + $X_2O_3$) | 0.01 to 20 | 0.05 to 5 |
| $M_{2/e}O$/ ($YO_2$ + WO + $Z_2O_5$ + $X_2O_3$) | 0 to 10 | 0 to 5 |
| $R_{2/f}O$/ ($YO_2WO$ + $Z_2O_5$ + $X_2O_3$) | 0.01 to 2.0 | 0.03 to 1.0 | wherein e and f are the weighted average valences of M and R, respectively.

In this first method, when no Z and/or W oxides are added to the reaction mixture, the pH is important and must be maintained at from about 9 to about 14. When Z and/or W oxides are present in the reaction mixture, the pH is not narrowly important for synthesis of the present crystalline material. In this, as well as the following methods for synthesis of the present material the $R_{2/f}O$/($YO_2$+WO+$Z_2O_5$+$X_2O_3$) ratio is important. When this ratio is less than 0.01 or greater than 2.0, impurity products tend to be synthesized at the expense of the present material.

A second method for synthesis of the present crystalline material involves a reaction mixture having an $X_2O_3$/$YO_2$ mole ratio of from about 0 to about 0.5, a crystallization temperature of from about 25° C. to about 250° C., preferably from about 50° C. to about 175° C., and two separate organic directing agents, i.e. the organic and additional organic directing agents, hereinafter more particularly described. This second method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, a combination of organic directing agent and additional organic directing agent (R), each hereinafter more particularly described, and solvent or solvent mixture, such as, for example, $C_1$–$C_6$ alcohols, $C_1$–$C_6$ diols and/or water, especially water, said reaction mixture having a composition, in terms of mole ratios of oxides, within the following ranges:

| Reactants | Useful | Preferred |
|---|---|---|
| $X_2O_3$/$YO_2$ | 0 to 0.5 | 0.001 to 0.5 |
| $X_2O_3$/($YO_2$ + $Z_2O_5$) | 0.1 to 100 | 0.1 to 20 |
| $X_2O_3$/($YO_2$ + WO + $Z_2O_5$) | 0.1 to 100 | 0.1 to 20 |
| Solvent/ ($YO_2$ + WO + $Z_2O_5$ + $X_2O_3$) | 1 to 1500 | 5 to 1000 |
| $OH^-$/$YO_2$ | 0 to 10 | 0 to 5 |
| ($M_{2/e}O$ + $R_{2/f}O$)/ ($YO_2$ + WO + $Z_2O_5$ + $X_2O_3$) | 0.01 to 20 | 0.05 to 5 |

-continued

| Reactants | Useful | Preferred |
|---|---|---|
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.1 to 2.0 | 0.12 to 1.0 | wherein e and f are the weighted average valences of M and R, respectively.

In this second method, when no Z and/or W oxides are added to the reaction mixture, the pH is important and must be maintained at from about 9 to about 14. When Z and/or W oxides are present in the reaction mixture, the pH is not narrowly important for crystallization of the present invention.

A third method for synthesis of the present crystalline material is where X comprises aluminum and Y comprises silicon, the crystallization temperature must be from about 25° C. to about 175° C., preferably from about 50° C. to about 150° C., and an organic directing agent, hereinafter more particularly described, or, preferably a combination of that organic directing agent plus an additional organic agent, hereinafter more particularly described, is used. This third method comprises preparing a reaction mixture containing sources of, for example, alkali or alkaline earth metal (M), e.g. sodium or potassium, cation if desired, one or more sources of aluminum and/or silicon, an organic (R) directing agent, hereinafter more particularly described, and a solvent or solvent mixture, such as, for example $C_1$–$C_6$ alcohols, $C_1$–$C_6$ diols and/or water, especially water, said reaction mixture having a composition, in terms of mole ratios of oxides, within the following ranges:

| Reactants | Useful | Preferred |
|---|---|---|
| $Al_2O_3/SiO_2$ | 0 to 0.5 | 0.001 to 0.5 |
| Solvent/$SiO_2$ | 1 to 1500 | 5 to 1000 |
| $OH^-/SiO_2$ | 0 to 10 | 0 to 5 |
| $(M_{2/e}O + R_{2/f}O)/(SiO_2 + Al_2O_3)$ | 0.01 to 20 | 0.05 to 5 |
| $M_{2/e}O/(SiO_2 + Al_2O_3)$ | 0 to 5 | 0 to 3 |
| $R_{2/f}O/(SiO_2 + Al_2O_3)$ | 0.01 to 2 | 0.03 to 1 | wherein e and f are the weighted average valences of M and R, respectively.

In this third method, the pH is important and must be maintained at from about 9 to about 14. This method involves the following steps:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) To the primary template mixture of step (1) add sources of oxides, e.g. silica and/or alumina such that the ratio of $R_{2/f}O/(SiO_2+Al_2O_3)$ is within the range of from about 0.01 to about 2.0.

(3) Agitate the mixture resulting from step (2) at a temperature of from about 20° C. to about 40° C., preferably for from about 5 minutes to about 3 hours.

(4) Allow the mixture to stand with or without agitation, preferably at a temperature of from about 20° C. to about 100° C., and preferably for from about 10 minutes to about 24 hours.

(5) Crystallize the product from step (4) at a temperature of from about 50° C. to about 175° C., preferably for from about 1 hour to about 72 hours. Crystallization temperatures higher in the given ranges are most preferred.

A fourth method for the present synthesis involves the reaction mixture used for the third method, but the following specific procedure with tetraethylorthosilicate the source of silicon oxide:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) Mix the primary template mixture of step (1) with tetraethylorthosilicate and a source of aluminum oxide, if desired, such that the $R_{2/f}O/SiO_2$ mole ratio is in the range of from about 0.05 to about 2.0.

(3) Agitate the mixture resulting from step (2) for from about 10 minutes to about 6 hours, preferably from about 30 minutes to about 2 hours, at a temperature of from about 0° C. to about 25° C., and a pH of less than 12. This step permits hydrolysis/polymerization to take place and the resultant mixture will appear cloudy.

(4) Crystallize the product from step (3) at a temperature of from about 25° C. to about 150° C., preferably from about 95° C. to about 110° C., for from about 4 to about 72 hours, preferably from about 16 to about 48 hours.

A fifth method includes adding an auxiliary organic to the reaction mixture prior to maintaining it for crystallization of the ultra-large pore crystalline material, such as prior to, during or immediately following addition of the other reaction mixture components. It is believed that the "primary template" in this method becomes the mixture of the auxiliary organic and the organic directing agent or organic directing agent mixture. This auxiliary organic must be selected from the group of organic compounds consisting of (1) aromatic hydrocarbons and amines of from 5 to 20 carbons and halogen- and $C_1$–$C_{14}$ alkyl-substituted derivatives thereof, (2) cyclic aliphatic hydrocarbons and amines of from 5 to 20 carbons and halogen- and $C_1$–$C_{14}$ alkyl-substituted derivatives thereof, (3) polycyclic aliphatic hydrocarbons and amines of from 6 to 20 carbons and halogen- and $C_1$–$C_{14}$ alkyl-substituted derivatives thereof, (4) straight and branched aliphatic hydrocarbons and amines of from 3 to 16 carbons and halogen-substituted derivatives thereof, and (5) combinations thereof. Of this group of organic compounds, the aromatic hydrocarbons (e.g. $C_6$–$C_{20}$), cyclic aliphatic hydrocarbons and polycyclic aliphatic hydrocarbons, and combinations thereof, are preferred.

In this group of auxiliary organic compounds for use in the present improved method, the halogen substituent in substituted derivatives may be, for example, bromine. The $C_1$–$C_{14}$ alkyl substituent in the substituted derivatives may be linear or branched aliphatic chains, such as, for example, methyl, ethyl, propyl, isopropyl, butyl, pentyl and combinations thereof. Nonlimiting examples of these auxiliary organics include, for example, p-xylene, trimethylbenzene, triethylbenzene and triisopropylbenzene.

With the inclusion of the auxiliary organic into the reaction mixture, the mole ratio of auxiliary organic- /YO₂ will be from about 0.05 to about 20, preferably from about 0.1 to about 10, and the mole ratio of auxiliary organic/R$_{2/f}$O will be from about 0.02 to about 100, preferably from about 0.05 to about 35. The useful range of temperatures for this crystallization is from about 25° C. to about 175° C., preferably from about 50° C. to about 150° C. Pore size and volume will vary with the amount and physical properties, e.g. structure, boiling point, density, polarity, etc., of the auxiliary organic used.

In each of the above methods, batch crystallization of the present crystalline material can be carried out under either static or agitated, e.g. stirred, conditions in a suitable reactor vessel, such as for example, polypropylene jars or teflon lined or stainless steel autoclaves. Crystallization may also be conducted continuously in suitable equipment. The total useful range of temperatures for crystallization is noted above for each method for a time sufficient for crystallization to occur at the temperature used, e.g. from about 5 minutes to about 14 days. Thereafter, the crystals are separated from the liquid and recovered.

When a source of silicon is used in the synthesis method, it is preferred to use at least in part an organic silicate, such as, for example, a quaternary ammonium silicate. Non-limiting examples of such a silicate include tetramethylammonium silicate and tetraethylorthosilicate.

Non-limiting examples of various combinations of W, X, Y and Z contemplated for the first and second synthesis methods of the present invention include:

| W  | X  | Y  | Z |
|----|----|----|---|
| —  | Al | Si | — |
| —  | Al | —  | P |
| —  | Al | Si | P |
| Co | Al | —  | P |
| Co | Al | Si | P |
| —  | —  | Si | — | including the combinations of W being Mg, or an element selected from the divalent first row transition metals, e.g. Mn, Co and Fe; X being B, Ga or Fe; and Y being Ge.

An organic directing agent for use in each of the above methods for synthesizing the present material from the respective reaction mixtures is an ammonium or phosphonium ion of the formula R₁R₂R₃R₄Q⁺, i.e.:

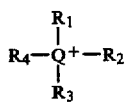

wherein Q is nitrogen or phosphorus and wherein at least one of R₁, R₂, R₃ and R₄ is aryl or alkyl of from 7 to about 36 carbon atoms, e.g. —C₇H₁₅, —C₁₀H₂₁, —C₁₂H₂₅, —C₁₄H₂₉, —C₁₆H₃₃ and —C₁₈H₃₇, or combinations thereof, the remainder of R₁, R₂, R₃ and R₄ being selected from the group consisting of hydrogen, alkyl of from 1 to 5 carbon atoms and combinations thereof. The compound from which the above ammonium or phosphonium ion is derived may be, for example, the hydroxide, halide, silicate, or mixtures thereof.

In the first and third methods above it is preferred to have an additional organic directing agent and in the second method it is required to have a combination of the above organic directing agent and an additional organic directing agent. That additional organic directing agent is the ammonium or phosphonium ion of the above directing agent formula wherein R₁, R₂, R₃ and R₄ together or separately are selected from the group consisting of hydrogen and alkyl of 1 to 5 carbon atoms and combinations thereof. Any such combination of organic directing agents go to make up "R" and will be in molar ratio of about 100/1 to about 0.01/1, first above listed organic directing agent/additional organic directing agent.

The particular effectiveness of the presently required directing agent, when compared with other such agents known to direct synthesis of one or more other crystal structures, is believed due to its ability to function as a template in the above reaction mixture in the nucleation and growth of the desired ultra-large pore crystals with the limitations discussed above. Non-limiting examples of these directing agents include cetyltrimethylammonium, cetyltrimethylphosphonium, octadecyltrimethylphosphonium, benzyltrimethylammonium, cetylpyridinium, myristyltrimethylammonium, dodecyltrimethylammonium and dimethyldidodecylammonium.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the crystalline material is molded, such as by extrusion, the crystals can be extruded before drying or partially dried and then extruded.

It may be desired to incorporate the new crystal composition with another material. Such materials include active and inactive materials and synthetic or naturally occurring zeolites as well as inorganic materials such as clays, silica and/or metal oxides such as alumina, titania and/or zirconia. The latter may be either naturally occurring or in the form of gelatinous precipitates or gels including mixtures of silica and metal oxides. Use of a material in conjunction with the new crystal, i.e. combined therewith or present during synthesis of the new crystal, which is active, may be selected to change the selectivity of the M41S in certain types of sensing devices. These materials may be incorporated with naturally occurring clays, e.g. bentonite and kaolin, to improve the crush strength of the M41S and to prevent the M41S substrates from breaking down into powder-like materials. These clay binders have been employed normally only for the purpose of improving the crush strength.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the new crystal can be composited with a porous matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

It may be desirable to provide at least a part of the foregoing matrix in colloidal form so as to facilitate extrusion of the bound M41S substrate components(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for water, cyclohexane, benzene and/or n-hexane, they are equilibrium adsorption values determined as follows:

A weighed sample of the adsorbent, after calcination at about 540° C. for at least about 1 hour and other treatment, if necessary, to remove any pore blocking contaminants, is contacted with the desired pure adsorbate vapor in an adsorption chamber. The increase in weight of the adsorbent is calculated as the adsorption capacity of the sample in terms of grams/100 grams adsorbent based on adsorbent weight after calcination at about 540° C. The present composition exhibits an equilibrium benzene adsorption capacity at 50 Torr and 25° C. of greater than about 15 grams/100 grams, particularly greater than about 17.5 grams/100 grams and more particularly greater than about 20 grams/100 grams.

A preferred way to do this is to contact the desired pure adsorbate vapor in an adsorption chamber evacuated to less than 1 mm at conditions of 12 Torr of water vapor, 40 Torr of n-hexane or cyclohexane vapor, or 50 Torr of benzene vapor, at 25° C. The pressure is kept constant (within about ±0.5 mm) by addition of adsorbate vapor controlled by a manostat during the adsorption period. As adsorbate is adsorbed by the new crystal, the decrease in pressure causes the manostat to open a valve which admits more adsorbate vapor to the chamber to restore the above control pressures. Sorption is complete when the pressure change is not sufficient to activate the manostat.

Another way of doing this for benzene adsorption data is on a suitable thermogravimetric analysis system, such as a computer-controlled 990/951 dupont TGA system. The adsorbent sample is dehydrated (physically sorbed water removed) by heating at, for example, about 350° C. or 500° C. to constant weight in flowing helium. If the sample is in as-synthesized form, e.g. containing organic directing agents, it is calcined at about 540° C. in air and held to constant weight instead of the previously described 350° C. or 500° C. treatment. Benzene adsorption isotherms are measured at 25° C. by blending a benzene saturated helium gas stream with a pure helium gas stream in the proper proportions to obtain the desired benzene partial pressure. The value of the adsorption at 50 Torr of benzene is taken from a plot of adsorption isotherm.

In the examples, percentages are by weight unless otherwise indicated.

EXAMPLE 1

A solution of 2.7 grams of $NaAlO_2$ (43.5% $Al_2O_3$, 30% $Na_2O$) in 146.9 grams of water was mixed with 34.5 grams of NaOH, 189.1 grams of cetyltrimethylammonium hydroxide solution prepared by contacting a 29 wt % N,N,N-trimethyl-1-hexadecanaminium chloride solution with an excess of hydroxide for halide resin, and 110.7 grams of Ultrasil (92% $SiO_2$). After stirring overnight it was loaded into a 600 cc autoclave and reacted at 150° C. with 400 rpm stirring for 72 hours. The mixture had the following relative molar composition:

0.25 moles $Al_2O_3$
10 moles $Na_2O$
36 moles $SiO_2$
2.5 moles $(CTMA)_2O$
362.5 moles $H_2O$ Following filtration of the mixture, the solid product which precipitated from the filtrate was recovered by filtration, washed with water, then calcined at 550° C. for 10 hours in air.

The calcined product proved to have a surface area of 1193 m²/g and the following equilibrium adsorption capacities in grams/100 grams anhydrous sorbent:

$H_2O$ 10.2
Cyclohexane >50
n-Hexane 48.9
Benzene 68.1

The X-ray diffraction pattern of the calcined product of this example may be characterized as including a very strong relative intensity line at 50.7±3.0 Angstroms d-spacing and a weak line at 30.7±1.0 Angstroms.

EXAMPLE 2

A 0.50 gram portion of a calcined product prepared as in Example 1 was added to a rapidly stirred solution of 10 grams chlorotrimethylsilane in 15 grams hexamethyldisiloxane. The mixture was refluxed under $N_2$ overnight, cooled, the reagents removed on a rotary evaporator, the product washed with two 10 mL portions of acetone and air dried to yield 0.53 grams of product.

A solid state magic angle spinning NMR spectrum of this product was obtained using 90 degree pulses at 1200 s intervals with proton decoupling. This spectrum showed peaks at 15 and 108 ppm. The peak at 15 ppm has been assigned to trimethylsilyl groups (T. Yanagisawa, et al., *Reactivity of Solids*, Vol. 5, 167 (1988)) and shows that the product has reacted. Integration of the two peaks showed that 17.9% of the silicons in the original product had been converted.

The internal pore volume of the trimethylsilylated product was compared to that of the starting material by both benzene sorption and argon physisorption. The total reduction in pore volume was measured as 48% by benzene and 34% by argon. The diameter of the TMS group was measured to be about 0.4–0.5 nm from CPK molecular models. An onion skin coating of TMS groups on the inside of the pore should, therefore, cause a decrease of 0.8–1.0 nm in pore diameter. The Horvath-Kowazoe transform of the argon isotherm shows the pore diameter to have decreased from 3.94 to 3.04 nm (0.90 nm) in agreement with what was predicted from the models.

Water sorption was measured before and after the chlorotrimethylsilane treatment. The calcined product of example 1 sorbed 10.0 weight percent water at 30° C. and 12.5 torr while the treated material sorbed 3.3 weight percent water. This demonstrates that trichloromethylsilane treatment increases the hydrophobic character of the novel crystalline material.

Example 2 demonstrates means of achieving pore size reduction using the treatment method of the invention.

EXAMPLE 3

A 0.50 gram portion of a product prepared as in Example 1 was added to a rapidly stirred solution of 15 mL hexamethyldisilazane in 15 grams hexamethyldisiloxane. The mixture was refluxed under $N_2$ overnight, cooled, the reagents removed on a rotary evaporator, the product washed with two 10 mL portions of acetone and air dried to yield 0.52 grams of product.

A solid state magic angle spinning NMR spectrum of this product obtained using 90 degree pulses at 1200 s intervals with proton decoupling. This spectrum showed peaks at 15 and −108 ppm. The peak 15 ppm has been assigned to trimethylsilyl groups (Id.) and shows that the product has reacted. Integration of the two peaks showed that 16.8% of the silicons in the original product had been converted. Within the experimental error of the Si-nmr experiment, the conversion by chlorotrimethylsilane and hexamethyldisilazane was the same.

EXAMPLE 4

Four hundred grams of cetyltrimethylammonium (CTMA) hydroxide solution, prepared by contacting a 29 wt % N,N,N-trimethyl-1-hexadecanaminium chloride solution with an excess of hydroxide-for-halide resin, was combined with two hundred grams of tetramethylammonium (TMA) silicate solution (10% by wt. silica, 1:1, TMA:Si) with stirring. Fifty grams of HiSil, a precipitated hydrated silica containing about 6 wt % free water and about 4.5 wt % bound water of hydration and having an ultimate particle size of about 0.02 micron, was added. The resulting mixture was placed in a polypropylene bottle and put into a steam box (about 100° C.) for 48 hours. The mixture had a composition in terms of moles per mole of $Al_2O_3$:

391.4 moles of $SiO_2$
71.4 moles of $(CTMA)_2O$
61.6 moles of $(TMA)_2O$
9144 moles of $H_2O$ The resulting solid product was recovered by filtration and dried in air at ambient temperature. The chemical analyses of the as-synthesized product were:

$SiO_2$ 23.7 wt %
$Al_2O_3$ 0.2 wt %
N 2.3 wt %
C 33.9 wt %
Ash, 1000° C. 22.1 wt %

EXAMPLE 5

A portion of the product from Example 4 was then calcined at 540° C. for one hour in nitrogen, followed by six hours in air. The benzene sorption for this material was 39.5 wt %.

EXAMPLE 6

One gram of the air dried product of Example 4 was mixed with one gram titanium tetraethoxide at room temperature for overnight. The mixture was then reacted with 5 grams of water for one hour. The product was calcined in nitrogen at 538° C. for one hour then air for 6 hours at 538° C. The benzene sorption at 30° C. was 25.0 wt %.

EXAMPLE 7

One gram of the air dried product of Example 4 was mixed with one gram aluminum tri-sec-butoxide at room temperature for overnight. The mixture was then reacted with 5 grams of water for one hour. The product was calcined in nitrogen at 538° C. for one hour then air for 6 hours at 538° C. The benzene sorption at 30° C. was 37.5 wt %.

EXAMPLE 8

Ten grams of the air-dried product from Example 4 was combined with Di-s-butoxyaluminoxy-triethyoxylsilane (DBALS), on a 1/1 gram for gram basis, and fifty grams of absolute ethanol and allowed to mix overnight. This mixture was then combined with one hundred grams of water and stirred for one hour. The resulting solid product was recovered by filtration and dried in air at temperature. The functionalized product was then calcined at 540° C. for one hour in nitrogen, followed by six hours in air.

Elemental Analysis of the product of untreated Example 4 is compared with the treated products of Examples 8–12 in Table 1 below.

EXAMPLE 9

Ten grams of the air-dried product from Example 4 was combined with Di-s-butoxyaluminoxy-triethoxysilane (DBALS) on a 1/1 gram for gram basis, and fifty grams of hexamethyldisiloxane and allowed to mix overnight. This mixture was combined with one hundred grams of water and stirred for one hour. The resulting solid product was recovered by filtration and dried in air at ambient temperature. The functionalized product was then calcined at 540° C. for one hour in nitrogen, followed by six hours in air.

EXAMPLE 10

Ten grams of the air-dried product from Example 4 was combined with Diethylphosphatoethyltriethoxysilane, on a 1/1 gram for gram basis, and fifty grams of absolute ethanol and allowed to mix overnight. This mixture was then combined with one hundred grams of water and stirred for one hour. The resulting solid product was recovered by filtration and dried in air at ambient temperature. The functionalized product was then calcined at 540° C. for one hour in nitrogen, followed by six hours in air.

EXAMPLE 11

Ten grams of the air-dried product from Example 4 was combined with Trimethylborate, on a 2/1 gram for gram basis, and fifty grams of absolute ethanol and allowed to mix overnight. This mixture was then combined with one hundred grams of water and stirred for one hour. The resulting solid product was recovered by filtration and dried in air at ambient temperature. The functionalized product was then calcined at 540° C. for one hour in nitrogen, followed by six hours in air.

EXAMPLE 12

Ten grams of the air-dried product from Example 4 was combined with 7.5 grams of aluminum isopropoxide and fifty grams of absolute ethanol and allowed to mix overnight. This mixture was then combined with one hundred grams of water and stirred for one hour. The resulting solid product was recovered by filtration and dried in air at ambient temperature. The functionalized product was then calcined at 540° C. for one hour in nitrogen, followed by six hours in air.

TABLE 1

| ELEMENTAL ANALYSES OF SYNTHESIS PRODUCTS | | | | | | | |
|---|---|---|---|---|---|---|---|
| | C | N | Si | Al | P | B | Ash, 1000° C. |
| Ex. 4 | 33.0 | 2.32 | 10.9 | 0.052 | — | — | 22.1 |
| Ex. 8 | — | — | 25.9 | 11.2 | — | — | 77.0 |
| Ex. 9 | — | — | 32.3 | 5.2 | — | — | 84.5 |
| Ex. 10 | — | — | 32.9 | — | 4.7 | — | 74.3 |
| Ex. 11 | — | — | 32.1 | — | — | 2.6 | 76.3 |
| Ex. 12 | — | — | 16.2 | 17.7 | — | — | 80.8 |

Examples 6–12 illustrate other types of functional groups which can be incorporated into the crystalline material using the method of the invention.

EXAMPLE 13

In this example, 1.65 grams of $NaAlO_2$ was added to 80 grams of cetyltrimethylammonium hydroxide (CTMAOH) solution, prepared by contacting a 29 wt. % N,N,N-trimethyl-1-hexadecanaminium chloride solution with a hydroxide-for-halide exchange resin. The mixture was stirred until the $NaAlO_2$ was completely dissolved. To this solution was added 40.0 grams of tetramethylammonium silicate solution (10 wt. % $SiO_2$), 10.0 grams of HiSil (90 wt. % $SiO_2$), and 6.01 grams of 1,3,5-trimethylbenzene. The resulting mixture was stirred at room temperature for several minutes. The gel was then loaded into a 300 ml autoclave and heated to 105° C. while stirring at 150 RPM. After about 4 hours of heating, the reaction was quenched with cold water, and the contents removed. The product was filtered and washed several times with warm (60°–70° C.) distilled water and with acetone. The final product was calcined at 538° C. in a $N_2$/air mixture for 8 hours. The gel reaction mixture had a composition in terms of moles per mole $Al_2O_3$ as follows:

1.25 moles $Na_2O$
27.8 moles $SiO_2$
5.1 moles $(CTMA)_2O$
2.24 moles $(TMA)_2O$
650 moles $H_2O$
6.91 moles 1,3,5-trimethylbenzene The calcined product of this example proved to have a surface area of 948.6 m²/g and a benzene adsorption capacity of 64.0 wt. %.

EXAMPLE 14

One gram of the product of Example 13 was mixed with one gram tetraethylorthosilicate at room temperature for overnight. The mixture was then reacted with 5 grams of water for one hour. The product was calcined in nitrogen at 538° C. for one hour then air for 6 hours at 538° C. The benzene sorption at 25° C. was 40.0 wt %. Since the crystalline material had an initial benzene sorption of 64.0 wt %, the pore volume was reduced by 37% suggesting that the pore diameter was reduced by 8 Angstroms.

EXAMPLE 15

To 18.7 gm of N-clear (Na-silicate) dissolved in 30.0 gm of distilled water was added 1.2 gm of sulfuric acid dissolved in 10 gm of water. After allowing the resulting mixture to stir for ten minutes, 16.77 gm cetyltrimethylammonium bromide in 50.2 gm $H_2O$ was added and the resulting gel was allowed to stir for 0.5 h. At this point 20 gm of water was added to the reaction. The gel was then crystallized under static, autogenous conditions in a polypropylene bottle (100 C). The resulting product was washed thoroughly with distilled water, dried and calcined to 538 C. The X-ray diffraction pattern of the calcined product of this example included a very strong relative intensity line at 33.2±2.0 Angstroms d-spacing and weak lines at 19.8±1.0 Angstroms and 17.5±1.0 Angstroms. The benzene sorption for this material was 50%.

EXAMPLE 16

0.5 gm of the product of Example 15 was combined with 10 mL of $(CH_3)_2S:BH_3$ in 20 mL of toluene. After stirring for ca. 5 minutes the solid was isolated by vacuum filtration, washed with n-hexanes and then washed with acetone. The dried product was then calcined in air to 538° C.

The X-ray diffraction pattern of the product of this example included a very strong relative intensity line at 32.4±2.0 Angstroms d-spacing and weak lines at 19.5±1.0 and 17.2±1.0 Angstroms. The benzene sorption was 41 wt. %. Since the crystalline material of Example 15 had a benzene sorption value of 50%, the pore volume of the material of the present example appears to have been reduced.

EXAMPLE 17

Three grams of calcined crystalline material prepared as described in Example 4 were added to a solution of 0.14 grams chromium acetate monohydrate in 10 grams water. This mixture was reacted overnight at room temperature. Excess moisture was removed under vacuum. The catalyst was dried in nitrogen at 250° C. for 5 hours then air at 600° C. for 9 hours. The temperature was lowered to 350° C. and the sample reduced in carbon monoxide for 30 minutes. The product was functionalized M41S.

EXAMPLE 18

The pore walls of the mesoporous crystalline material are functionalized for protein attachment by coupling through two oxygen atoms, one oxygen coupled to the pore walls and one oxygen coupled to the protein.

The mesoporous crystalline material M41S in an amount of 500 mg is suspended in a solution of 2 mg/ml $NaBH_4$ in 1MNaOH. This suspension is incubated with 1–5 volumes of bisepoxide (bisoxiran,oxiran,butandiodiglycidyl ether) under vigorous shaking at 25° C. for about five hours. The bisepoxide phase disappears. The resulting oxiran activated M41S is removed from suspension by centrifugation washed thoroughly with water, and again centrifuged out.

The oxiran activated M41S is resuspended in a solution of 2 mg/ml $NaBH_4$, 1M NaOH and incubated with ovalbumin protein overnight.

Excess oxiran groups in the suspension are then inactivated with an excess of ethylamine, and the suspension is subjected to successive washes as follows:
1. neutral wash—$H_2O$ 2. high pH wash—0.1M potassium borate, pH 8.0
3. high salt—0.5M NaCl
4. low pH wash—0.1M potassium acetate, pH 4.0
5. high salt—0.5M NaCl
6. neutral wash—H$_2$O, pH 7.0

After the protein is coupled to the surface, it can be used for direct coupling to antibodies through the NH$_2$ groups on the antibody using an optical indicator such as fluorescence or a radioactive label.

Antibodies can also be coupled to the surface through the following groups: carbonyldiimidazole, cyanogen bromide, glutaraldehyde, hydroxysuccinimide and tosyl chloride which are first fastened to the pore walls by appropriate functionalization chemistry know in the art.

EXAMPLE 19

A non-composite membrane is prepared by following the procedure outlined in U.S. Pat. Nos. 5,019,263, 5,069,794 and 5,100,596. Accordingly, a non-porous surface is contacted with a chemical mixture capable of forming the desired crystalline material under crystallization conditions as described in Pat. Nos. 5,057,296 and 5,108,725. After a period of time under suitable conditions, a cohesive membrane of crystalline material forms on the non-porous substrate surface. The thickness dimension of the membrane may vary from about 0.02 microns to about 50 microns, preferably about 0.1 micron to about 2 microns depending upon the length of time the surface is contacted with the chemical mixture and the amount of mixture provided. Other means such as varying the temperature or the ratio of crystallization mixture to forming surface area are also effective in adjusting the membrane thickness to a desired dimension.

The time of contacting of the surface with the reaction mixture may be from about 0.5 hrs. to about 72 hrs., preferably from about 1 hr to about 10 hrs. and at a temperature ranging from about 25° C. to about 175° C., preferably from about 50° C. to about 150° C.

After the desired period of time, the substrate, now coated with crystalline material, is removed from contact with the chemical mixture, washed with distilled water and allowed to dry. The layer of crystalline material may be removed from the non-porous surface by various means depending upon the material chosen for the forming surface. The layer may be separated from polymeric surfaces, for example, by mechanical means such as careful scraping or peeling. Removal from metal surfaces may be accomplished with the use of solvents such as acetone, or by dissolving the metal with acid such as aqueous hydrochloric or nitric acid. With a support consisting of metal or metallized material such as aluminum or glass or teflon, treatment with an aqueous mineral acid can be employed.

The membrane material may also be calcined before or after removal from the substrate, for example, in an inert atmosphere or in air at a temperature ranging from about 150° C. to about 700° C. for about 0.5 hrs. to about 15 hrs.

A 0.50 gram portion of the membrane is contacted with a rapidly stirred solution of 10 grams chloromethylphenanthrolinesilane reagent in 15 grams hexamethyldisiloxane. The mixture is refluxed under N$_2$ overnight, cooled, the reagents removed on a rotary evaporator, the product washed with two 10 mL portions of acetone and dried to yield a membrane of crystalline material with phenanthroline functionalized within the pores.

EXAMPLE 20

The phenanthroline-functionalized crystalline membrane prepared in Example 19 is contacted with an aqueous sample for the detection of Fe$^{+3}$ ions. After contact with the sample, the presence of Fe$^{+3}$ ions in the membrane is detected using Spectrophotometry.

EXAMPLE 21

A functionalized membrane is prepared as in Example 19 except that the membrane is functionalized with dimethylglyoxine. The membrane is used for the detection of nickel using the method described in Example 20.

EXAMPLE 22

A non-composite membrane is prepared as in Example 19 and functionalized with porphyrin which has been complexed with Rh, Fe, Cu or Mg. The Rh containing sensor is used to detect carbon monoxide. The Fe-containing sensor is used to detect carbon dioxide. The Cu containing sensor is used to detect NO. The Mg containing sensor is used to detect formaldehyde. These detections make use of optical changes in visible light, UV (shift in Soret band) or IR for detection.

EXAMPLE 23

Tunable Sensor—SAW Device

The product of Example 1 is dip coated from alcohol solution or press coated to a thickness of one micron on a quartz piezoelectric substrate with a transduction means.

The presence of benzene is detected and quantified using this tunable sensor. A benzene sorption isotherm is obtained by standard procedures as described by Beck et al., "A New Family of Mesoporous Molecular Sieves Prepared with Liquid Crystal Templates," *J. Am. Chem. Soc.* 114, 10834–10843 (1992) and compared with standardized isotherms.

Figure 5:
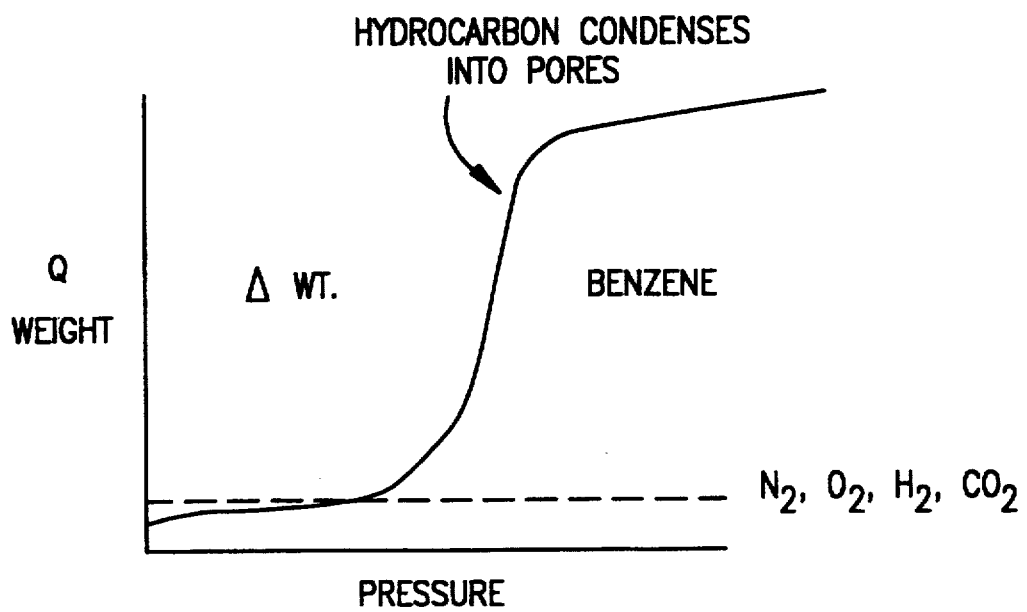
FIG. 5 is a graph depicting the absorption of hydrocarbon.

A gas stream suspected of containing benzene is contacted with the sensor. When the sensor is subjected to this gas stream the weight of the M41S layer increases as benzene is absorbed. The weight change is detected by a wavelength change in the piezoelectric substrate and recorded by a transducer means. Standardized benzene sorption isotherms are measured at 25° C. as described by Beck, et al., *J. Am. Chem. Soc.* 114, 10834–10843 (1992). FIG. 5 illustrates the isotherm.

Weight changes occur when the hydrocarbon reaches a certain level so that breakthrough beyond that level can be determined. Meanwhile, weakly absorbing gases such as He, N$_2$, O$_2$ and methane remain level and do not interfere. Variables influencing the hydrocarbon absorption include temperature and also pore size of the crystalline material which can be determined and factored into a standardized isotherm.

Using this sensor device, the level of benzene or other hydrocarbons for which adsorption properties have been measured can be determined when in mixtures with light gases, such as Ne, He, CO. Although the sensor is effective in the presence of H$_2$O, the absorption of H$_2$O can be reduced by functionalizing the mesoporous crystalline material with silanes or silazanes to render it hydrophobic.

Since the benzene can move freely into and out of the pores of the crystalline coating, the detection can be continuous thereby monitoring benzene levels over a period of time.

EXAMPLE 24

Fiber-Optic Chemical Sensor

A bifurcated fiber-optic cable is supplied as shown in FIG. 3.

Mesoporous crystalline material is prepared as in Example 1 and functionalized with a fluorescent dye such as rhodamine B as described in Example 2. A layer of the functionalized crystalline material is immobilized on the tip of the bifurcated fiber-optic cable in a thickness of 0.1 micron to 2 microns.

The device is retained in a closed container and exposed for about 0.1 second up to about one minute to the ambient atmosphere of a coal mine. The fiber optic cable is pumped with 308 nm zenon chloride exemer laser at about 100 millijoules to about 5 joules/pulse, preferably about 0.5 to 3 joules/pulse power and the luminescence monitored. The presence of luminescence indicates that a polar compound, e.g. ammonia or carbon monoxide is present and has been absorbed by the crystalline material. The device can be supplied with an alarm means to indicate whether noxious gases have exceeded safe levels.

EXAMPLE 25

Evanescent Field Fiber-Optic Chemical Sensor

A single fiber optic cable having a thickness of 50 to 500 um is supplied as shown in FIG. 2. The mesoporous crystalline material prepared and functionalized with rhodamine B as described in Example 24 is immobilized as a cladding layer in a thickness of about 0.1 micron to 2 microns arranged as two 100–500 micron segments surrounding a fiber optic cable which serves as a core.

The sensor is retained in a closed container until exposure to an atmosphere to be tested. When pumped with light as described in Example 24, the light propagates freely through the core and an evanescent field forms at the core-cladding interface exciting luminescence in the functionalized cladding. If a specified gas such as carbon monoxide has been absorbed by the sensor, the presence of the gas will be indicated by a precalibrated change in the fluorescence.

What is claimed is:

1. A sensor device comprising an inorganic, porous, non-layered crystalline phase material exhibiting, after calcination, an X-ray diffraction pattern with at least one peak at a d-spacing greater than about 18 Angstrom Units with a relative intensity of 100 and having a benzene sorption capacity of greater than 15 grams benzene per 100 grams of anhydrous crystal at 50 torr and 25° C., and a means for detecting, the device capable of detecting an event selected from the group consisting of sorption of a gas, change in pH, presence of metal ions, reaction between co-members of a biological affinity pair, presence of Lewis acid and presence of a Lewis base, said event occurring in the crystalline material.

2. The device of claim 1 wherein the crystalline phase material has been modified by contacting with a treatment composition comprising $M'X'Y'_n$ wherein M' is selected from a group consisting of Periodic Table Groups IIA, IIIA, IVA, VA, VIA, VIIIA, IB, IIB, IIIB, IVB, VB and VIB;

X' is selected from a group consisting of halides, hydrides, alkoxides of 1 to about 6 carbon atoms alkyl of $C_{1-18}$, alkenyl of $C_{6-18}$, aryl of $C_{6-18}$, aryloxide of $C_{6-18}$, sulfonates, nitrates and acetates;

Y' is selected from a group consisting of X', amines, phosphines, sulfides, carbonyls and cyanos; and n = 1–5; said contacting occurring under sufficient conditions so that the crystalline phase material functionalized.

3. The device of claim 2 wherein the crystalline material is contacted with the treatment composition before organics are removed by calcination or low temperature organics extraction.

4. The device of claim 2 wherein the crystalline material is contacted with the treatment composition after organics are removed by calcination or low temperature organics extraction.

5. The device of claim 1 wherein the crystalline material is as-synthesized.

6. The device of claim 1 wherein the crystalline material is calcined.

7. The device of claim 1 wherein the crystalline material has been subjected to low temperature organics extraction at less than 150° C.

8. The device of claim 1 wherein the crystalline material comprises an inorganic, porous crystalline phase material having a hexagonal arrangement of uniformly-sized pores at least about 13 Angstroms in diameter and exhibiting, after calcination, a hexagonal electron diffraction pattern that can be indexed with a $d_{100}$ value greater than 18 Angstrom Units.

9. The device of claim 1 wherein the means for detecting is selected from the group consisting of surface acoustic wave, fiber optic, electrochemical, spectroscopic, autoradiographic and semiconductor elements.

10. The device of claim 1 wherein the material has pores which have been adjusted to a predetermined shape and size.

11. The device of claim 1 wherein the material contains a selective detecting component.

12. The sensor device of claim 11 wherein the selective detecting element is supported unattached within the pores of the material.

13. The sensor device of claim 11 wherein the selective detecting component is covalently bonded within the pores of the material.

14. The device of claim 11 wherein the selective detecting component is hydrogen-bonded within the pores of the material.

15. The device of claim 11 wherein the selective detecting component is coordinatively attached within the pores of the material.

16. The device of claim 11 wherein the selective detecting component is selected from the group consisting of ionophores, Lewis bases, Lewis acids, fluorophores, dyes, $M'Y'_n$ and a member of a biological binding pair.

17. A method for detecting a compound selected from the group consisting of a gas, hydrogen ions (pH), metal ions, a co-member of a biological affinity pair, a Lewis acid and a Lewis base comprising contacting a medium containing the compound with a sensor device which comprises an inorganic, porous, non-layered crystalline phase material exhibiting, after calcination, an X-ray diffraction pattern with at least one peak at a d-spacing greater than about 18 Angstrom Units with a relative intensity of 100 and having a benzene sorption capacity of greater than 15 grams benzene per 100 grams of anhydrous crystal at 50 torr and 25° C. and detecting the compound in the crystalline material with a means for detecting.

18. The device of claim 17 wherein the crystalline phase material has been modified by contacting with a treatment composition comprising M'X'Y'$_n$ wherein
M' is selected from a group consisting of Periodic Table Groups IIA, IIIA, IVA, VA, VIA, VIIIA, IB, IIB, IIIB, IVB, VB and VIB;
X' is selected from a group consisting of halides, hydrides, alkoxides of 1 to about 6 carbon atoms alkyl of C$_{1-18}$, alkenyl of C$_{6-18}$, aryl of C$_{6-18}$, aryloxide of C$_{6-18}$, sulfonates, nitrates and acetates;
Y' is selected from a group consisting of X', amines, phosphines, sulfides, carbonyls and cyanos; and
n=1-5; said contacting occurring under sufficient conditions so that the crystalline phase material functionalized.

19. The device of claim 18 wherein the crystalline material is contacted with the treatment composition before organics are removed by calcination or low temperature organics extraction.

20. The device of claim 18 wherein the crystalline material is contacted with the treatment composition after calcination.

21. The device of claim 17 wherein the crystalline material is as-synthesized.

22. The device of claim 17 wherein the crystalline material is calcined.

23. The device of claim 17 wherein the crystalline material is subjected to low temperature organics extraction at less than 150° C.

24. The method of claim 17 wherein the means for detecting physical or chemical changes is selected from the group consisting of surface acoustic wave, fiber optic, electrochemical, spectroscopic, autoradiographic and semiconductor elements.

25. The method of claim 17 wherein the material has pores which have been adjusted to a predetermined shape and size.

26. The method of claim 17 wherein the material contains a selective detecting component.

27. The method of claim 26 wherein the selective detecting element is unattached within the pores of the material.

28. The method of claim 26 wherein the selective detecting component is covalently bonded within the pores of the material.

29. The method of claim 26 wherein the selective detecting component is hydrogen-bonded within the pores of the material.

30. The method of claim 26 wherein the selective detecting component is coordinatively attached within the pores of the material.

31. The method of claim 26 wherein the selective detecting component is selected from the group consisting of ionophores, Lewis bases, Lewis acids, fluorophores dyes, M'Y'$_n$ and a member of a biological binding pair.

32. The method of claim 17 wherein the method detects a gas, the means for detecting comprises a piezoelectric crystal and the gas is selected from the group consisting of pyridine, thiophenes, mercaptans, furans, benzene, methane, carbon dioxide, carbon monoxide, NO$_x$ and SO$_x$.

33. The method of claim 17 wherein the method detects a gas, the means for detecting comprises a fiber optic cable and the gas is selected from the group consisting of NH$_3$, HCN, CO$_2$, CO, SO$_2$, NO$_x$, O$_2$, H$_2$O$_2$, formaldehyde, organoamines, thiophenes, pyridine, piperidine and pyrrolidine.

34. The method of claim 17 wherein the method detects hydrogen ions (pH), the means for detecting comprises a fiber optic cable and the crystalline material contains a pH indicator dye.

35. The method of claim 17 wherein the method detects metal ions, the means for detecting the presence of metal ions comprises potentiometric electrodes or spectroscopy and the crystalline material contains an ionophore selected from the group consisting of phenanthroline, porphyrins, salens, salophens, cryptands, cyclams, crown ethers and dimethylgloxine.

36. The method of claim 17 wherein the method detects a co-member of a biological affinity pair, the means for detecting comprises a member of the group consisting of potentiometric electrodes, autoradiography and fiber optic cable and one co-member of a biological affinity pair selected from the group consisting of antigen-antibody, hapten-antibody, polysaccharide-receptor, monosaccharide-receptor, glycoprotein-receptor, glycolipid-lectin, enzyme-substrate, enzyme-cofactor, enzyme inhibitor-enzyme, neurotransmitter-neuroreceptor, hormone-neural receptor and single strand nucleic acid complementary strand nucleic acid.

37. The method of claim 17 wherein the method detects a Lewis acid or base, the means for detecting comprises spectroscopy and the crystalline material contains sites selected from the group consisting of Lewis acids aluminum, copper, cobalt and transition metals and Lewis bases which are nitrogen-containing polymer pyrroles or amines.

38. A sensor device for sensing a gas selected from the group consisting of pyridine, thiophenes, mercaptans, furans, benzene, methane, carbon dioxide, carbon monoxide, NO$_x$ and SO$_x$ comprises M41S crystalline phase material and a detecting means comprising a piezoelectric crystal.

39. A sensor device for sensing a gas selected from the group consisting of NH$_3$, HCN, CO$_2$, CO, SO$_2$, NO$_x$, O$_2$, H$_2$O$_2$, formaldehyde, organoamines, thiophenes, pyridine, piperidine and pyrrolidine comprises M41S crystalline phase material functionalized with an indicator molecule and a detecting means comprising a fiber optic cable.

40. A sensor device for sensing a change in pH comprises M41S crystalline phase material functionalized with a pH indicator dye and a detecting material means comprising a fiber optic cable.

41. A sensor device for sensing the presence of metal ions comprises M41S phase material containing an ionophore selected from the group consisting of phenanthroline, porphyrins, salen, salophen, cryptand, cyclam, crown ether and dimethylgloxine and a detecting means comprising potentiometric electrodes or spectroscopy.

42. A sensor device for sensing a reaction between co-members of a biological affinity pair comprises M41S crystalline phase material containing one co-member of the biological pair, the pair selected from the group consisting of antigen-antibody, hapten-antibody, polysaccharide-receptor, monosaccharide-receptor, glycoprotein-receptor, glycolipid-lectin, enzyme-substrate, enzyme-cofactor, enzyme inhibitor-enzyme, neurotransmitter-neuroreceptor, hormone-neural receptor and single strand nucleic acid-complementary strand nucleic acid; and a detecting means comprising a member of the group consisting of electrochemical, autoradiographic and fiber optic measuring components.

43. A sensor device for detecting Lewis acids or Lewis bases comprises M41S crystalline phase material functionalized with sites selected from the group consisting of Lewis acids which are aluminum, copper, cobalt and transition metals and Lewis bases which are nitrogen-containing polymer polypyrroles and amines, and a detecting means comprising spectroscopy.

* * * * *

UNITED STATES PATENT AND TRADEMARK OFFICE
CERTIFICATE OF CORRECTION

PATENT NO. : 5,364,797
DATED : November 15, 1994
INVENTOR(S) : D.H. Olson et al.

It is certified that error appears in the above-indentified patent and that said Letters Patent is hereby corrected as shown below:

Col. 32, claim 2, line 7, insert --is-- before "functionalized".

Col. 33, claim 18, line 17, insert --is-- before "functionalized".

Signed and Sealed this

Fourteenth Day of March, 1995

Attest:

BRUCE LEHMAN

Attesting Officer  Commissioner of Patents and Trademarks